United States Patent
Liu et al.

(10) Patent No.: US 11,967,250 B2
(45) Date of Patent: Apr. 23, 2024

(54) EYEPIECE, EYE SIMULATOR DEVICE, MANNEQUIN SIMULATOR AND TRAINING METHOD

(71) Applicant: TELLYES SCIENTIFIC INC., Tianjin (CN)

(72) Inventors: Yanfei Liu, Tianjin (CN); Zhaoqun Liu, Tianjin (CN); Jun Lu, Tianjin (CN); Jibin Zhou, Tianjin (CN); David N. Broussard, Lorena, TX (US); Charles G. Miller, Allison Park, PA (US); Jerry Woods, Pittsburgh, PA (US); Clifford D. Olmstead, Allison Park, PA (US)

(73) Assignee: TELLYES SCIENTIFIC INC. (CN)

( * ) Notice: Subject to any disclaimer, the term of this patent is extended or adjusted under 35 U.S.C. 154(b) by 610 days.

(21) Appl. No.: 17/273,242

(22) PCT Filed: Sep. 5, 2018

(86) PCT No.: PCT/CN2018/104059
§ 371 (c)(1),
(2) Date: Mar. 3, 2021

(87) PCT Pub. No.: WO2020/047762
PCT Pub. Date: Mar. 12, 2020

(65) Prior Publication Data
US 2021/0192978 A1    Jun. 24, 2021

(51) Int. Cl.
G09B 23/32   (2006.01)
A61B 34/10   (2016.01)
(Continued)

(52) U.S. Cl.
CPC .............. *G09B 23/32* (2013.01); *A61B 34/10* (2016.02); *G06T 11/001* (2013.01); *G06T 15/00* (2013.01);
(Continued)

(58) Field of Classification Search
CPC ...... G09B 23/30; G09B 23/32; G09B 23/281; A63H 3/38; A63H 3/40; A63H 3/42
(Continued)

(56) References Cited

U.S. PATENT DOCUMENTS 2,989,819 A * 6/1961 Songer .................... A63H 3/38
446/343
3,177,593 A * 4/1965 Loeb ..................... G09B 23/34
434/271
(Continued)

FOREIGN PATENT DOCUMENTS

| CA | 2963116 | 6/2017 |
|---|---|---|
| CN | 101745230 | 6/2010 |

(Continued)

OTHER PUBLICATIONS

International Search Report and Written Opinion for PCT/CN2018/104059 dated May 30, 2019.

*Primary Examiner* — Joseph B Baldori
(74) *Attorney, Agent, or Firm* — McDonald Hopkins LLC

(57) ABSTRACT

Disclosed is an eye simulator device, wherein same is a medical training aid and includes: an eyepiece having a display configured to project at least one image onto or through a convex shaped front surface of a simulated eyeball of the eyepiece; a support configured to hold the eyepiece; a simulated eyelid pivotally attached to the support; and an actuator assembly having an actuator arm and an electromagnetic (EM) coil in connection with the actuator arm, so as to control a motion of the simulated eyelid, which allows
(Continued)

to more realistically mimic the eye, and to more intuitively mimic a motion change of the eye, and it is illustratable to show a change process of the eye by projecting an eye condition, making it easier for a student to understand.

12 Claims, 10 Drawing Sheets

(51) Int. Cl.
*G06T 11/00* (2006.01)
*G06T 15/00* (2011.01)
*H04N 23/71* (2023.01)

(52) U.S. Cl.
CPC ........ *H04N 23/71* (2023.01); *A61B 2034/105* (2016.02)

(58) Field of Classification Search
USPC ......... 434/267, 270, 271; 446/391, 392, 393
See application file for complete search history.

(56) References Cited

U.S. PATENT DOCUMENTS

| | | | | |
|---|---|---|---|---|
| 3,905,130 A * | 9/1975 | Gordon | ............... | G09B 23/32 446/175 |
| 5,000,714 A * | 3/1991 | Su | ............... | A63H 3/38 446/485 |
| 5,004,443 A * | 4/1991 | Su | ............... | A63H 3/38 446/485 |
| 5,221,208 A * | 6/1993 | Alexander | ............ | G09B 23/30 434/271 |
| 5,415,579 A | 5/1995 | Pracas | | |
| 5,900,923 A * | 5/1999 | Prendergast | ........... | G09B 23/28 351/221 |
| 6,576,013 B1 | 6/2003 | Budman et al. | | |
| 8,007,340 B2 * | 8/2011 | Sip | ............... | A63H 3/38 446/337 |
| 8,062,092 B2 * | 11/2011 | Yang | ............... | A63H 3/40 446/337 |
| 8,113,907 B2 * | 2/2012 | Liu | ............... | A63H 3/40 396/428 |
| 8,202,138 B2 * | 6/2012 | Lai | ............... | A63H 3/40 446/389 |
| 8,251,770 B2 * | 8/2012 | Jin | ............... | A63H 3/38 446/131 |
| 8,333,635 B2 * | 12/2012 | Su | ............... | A63H 3/40 446/389 |
| 8,337,272 B2 * | 12/2012 | Su | ............... | A63H 3/38 446/389 |
| 8,651,916 B2 * | 2/2014 | Irmler | ............... | A63H 3/40 446/389 |
| 9,776,097 B2 * | 10/2017 | Smoot | ............... | A61F 2/141 |
| 10,083,631 B2 * | 9/2018 | Forte | ............... | G09B 23/30 |
| 10,360,859 B1 * | 7/2019 | Heilbron | ............... | G09G 3/32 |
| 11,257,463 B2 * | 2/2022 | Flamand | ............... | G09G 3/2003 |
| 11,263,924 B2 * | 3/2022 | Flamand | ............... | G09G 3/3413 |
| 2008/0139082 A1 * | 6/2008 | Schnuckle | ............ | G09B 23/22 446/392 |
| 2008/0191827 A1 * | 8/2008 | Hsiao | ............... | A63H 3/40 335/229 |
| 2009/0305605 A1 * | 12/2009 | Lin | ............... | A63H 3/40 446/342 |
| 2010/0015885 A1 * | 1/2010 | Chang | ............... | A63H 3/38 446/392 |
| 2010/0041306 A1 * | 2/2010 | Yang | ............... | A63H 3/40 446/343 |
| 2012/0081663 A1 * | 4/2012 | Schmid | ............... | A61B 3/11 351/205 |
| 2014/0127663 A1 | 5/2014 | Eggert et al. | | |
| 2017/0039894 A1 * | 2/2017 | Kirchhoff | ............. | G09B 23/32 |
| 2018/0286286 A1 * | 10/2018 | Flamand | ............... | G09B 23/32 |
| 2021/0315685 A1 * | 10/2021 | Fan | ............... | G09B 23/30 |

FOREIGN PATENT DOCUMENTS

| | | |
|---|---|---|
| CN | 202355835 | 8/2012 |
| CN | 103055514 | 4/2013 |
| CN | 103055514 A | 4/2013 |
| CN | 103117017 A | 5/2013 |
| CN | 103959357 | 7/2014 |
| CN | 103959357 A | 7/2014 |
| CN | 205751327 U | 11/2016 |
| CN | 106426196 | 2/2017 |
| CN | 206471044 U | 9/2017 |
| JP | H05205030 | 8/1993 |

* cited by examiner

EYEPIECE, EYE SIMULATOR DEVICE, MANNEQUIN SIMULATOR AND TRAINING METHOD

CROSS-REFERENCE TO RELATED APPLICATIONS(S)

This is a national stage application filed under 37 U.S.C. 371 based on International Patent Application No. PCT/CN2018/104059, filed Sep. 5, 2018, the disclosure of which is incorporated herein by reference in its entirety.

BACKGROUND

Embodiments of the disclosure relate to an eye simulator device, and in particular, to an eyepiece, an eye stimulator device, a mannequin simulator and a training method.

Some medical simulators including a simulated eyeball, are used for medical practitioners to train medical conditions and medical symptoms related to an eye. Conventional eye assemblies may be limited in function, reliability, and realistic operation. For example, conventional eye assemblies need to be operated with pneumatic actuators or electric gear motors that may generate noise interference and may lead to premature mechanical failure. Further, the conventional simulated eyeball does not allow to operate splaying a simulated eyelid manually (the simulated eyelid should be forced to splay for examination), and some components thereof can only be allowed to operate opening/closing the eye and to change a pupil, but fail to track an eye motion as some object moves. Yet, the convention simulated eyeball is usually complicated and big, resulting in inconvenient use.

SUMMARY

In order to solve the problem that the conventional simulated eyeball does not allow a medical practitioner to spray a simulated eyelid manually, which cannot mimic a real situation that an eyelid is forced to open, the present disclosure provides an eye simulator device.

The present disclosure involves an eye simulator device, which has an actuator arm and an electromagnetic (EM) coil in connection with the actuator arm to control a simulated eyelid motion of an eyepiece on the eye simulator device; and the eye simulator device further include a display which is configured to project an image on a simulated eyeball of the eyepiece or on a front surface of the simulated eyeball of the eyepiece. The eye simulator device may be configured to generate a simulated eyelid motion or an eye condition (by projection), which can mimic the eye condition for the medical practitioner.

The present disclosure provides an eyepiece, including:
a simulated eyeball having an eyeball front surface; and
a display, configured to project at least one image on or through the eyeball front surface, wherein the at least one image is a 2D representation or a 3D representation of a human eye.

In a preference, the eyepiece further includes an image sensor, disposed in line with an axis of the display, or offset from the axis of the display.

Further in a preference, the image sensor is configured to detect at least one of light brightness, light intensity, light motion, a light wavelength, temperature, and pressure.

In a preference, the at least one image includes at least one of a sclera, an iris, and a pupil.

The present disclosure further provides an eye simulator device, including the eyepiece, and the eye simulator device further includes:
a support, configured to hold the eyepiece;
a simulated eyelid, pivotally attached to the support and configured to match with the simulated eyeball; and
an actuator assembly, including an actuator arm and an electromagnetic (EM) coil in connection with the actuator arm, the actuator arm being in a mechanical connection with the simulated eyelid so as to drive the simulated eyelid to generate an eye motion.

In a preference, the eye simulator device further includes a base which is a housing of the actuator assembly, and where the support extends from the base.

In a preference, the eye simulator device further includes an electrical circuitry which is in connection with the actuator assembly and the display and configured to generate a bi-polar pulse with a modulated signal. Further, in a preference, the eye simulator device includes a position sensor configured to record a position of the simulated eyelid and to transmit the position of the simulated eyelid to the electrical circuitry.

In a preference, the eye simulator device further includes a centering magnet configured to force the actuator arm to a default position.

The present disclosure further provides a mannequin simulator, including at least one the eye simulator device, and the eye simulator device is arranged in at least one eye socket of the mannequin simulator.

The present disclosure further provides a training method for a medical practitioner, including:
providing any the eye simulator device according to any one of claims 5 to 9;
projecting at least one image to the eyepiece to generate an eye condition via the display, wherein the at least one image is a 2D representation or a 3D representation of a human eye and includes at least one of a sclera, an iris, and a pupil, and the eye condition includes one of a reddening of the sclera, a yellowing of the sclera, and a cloudiness of the sclera;
driving the actuator assembly to cause the simulated eyelid to generate an eye motion, wherein the eye motion includes one of eye closing, eye opening, eye blinking, and position offsetting of the simulated eyelid; and
causing the display to generate an obvious pupil motion by using the image sensor to track an object motion.

In a preference, the training method for a medical practitioner, further includes: in response to an operation of an operator, causing the display to generate the eye condition, causing the simulated eyelid to generate the eye motion; and causing the display to generate the obvious pupil motion.

Comparing to the prior art, advantages of the present disclosure lie in that: not only an eye opening/closing motion may be realized, but also the simulated eyelid may be sprayed manually, in addition, a position of the simulated eyelid may be controlled, which allows to mimic the eye more realistic, and to mimic a motion change of the eye more intuitive. And, it is able to project at least one image onto or through a front surface of an eyeball of an eye part so as to realize an eye condition, and it is further able to realize that the eye moves as an object moves. In the present disclosure, the eye simulator device is relatively simple in structure, and may be disposed in any eye socket of a mannequin simulator, which makes product standardization significantly, and the eye simulator device may be widely used in any kind of mannequin, which makes the mannequin more realistic, and makes the medical practitioner understand a motion change of a human eye more intuitive.

In which: 100—eye simulator device; 102—base; 104—electrical circuit; 106—actuator assembly; 108—eyepiece; 110—base first (front) side; 112—base second (back) side; 113 screw(s); 114—base top; 116—base bottom; 118—support; 120—simulated eyeball; 122—support first end; 124—support second end; 126—base longitudinal axis; 128—base latitudinal axis; 130—simulated eyelid; 132—pivot; 134—interior surface of the simulated eyelid; 136—exterior surface of the simulated eyelid; 138—first side of the simulated eyelid; 140—second side of the simulated eyelid; 142—first side of the support; 144—second side of the support; 146—simulated lens; 148—sclera; 150—iris; 152—pupil; 154—display; 156—convex shaped front surface; 158—image sensor; 160—driver controller; 162—first sector; 164—second sector; 166—EM coil; 168—actuator arm; 170—torque magnet; 172—EM coil inner surface; 174—EM coil outer surface; 176—connector portion; 178—arm portion; 180—centering magnet; 182—position sensor; 186—electrical power source; 188—driving control circuit.

DETAILED DESCRIPTION

The following description is of exemplary embodiments that are presently contemplated for carrying out the present disclosure. This description is not to be taken in a limiting sense, but is made merely for the purpose of describing the general principles and features of the present disclosure. The scope of the present disclosure is not limited by this description.

Figure 1A:
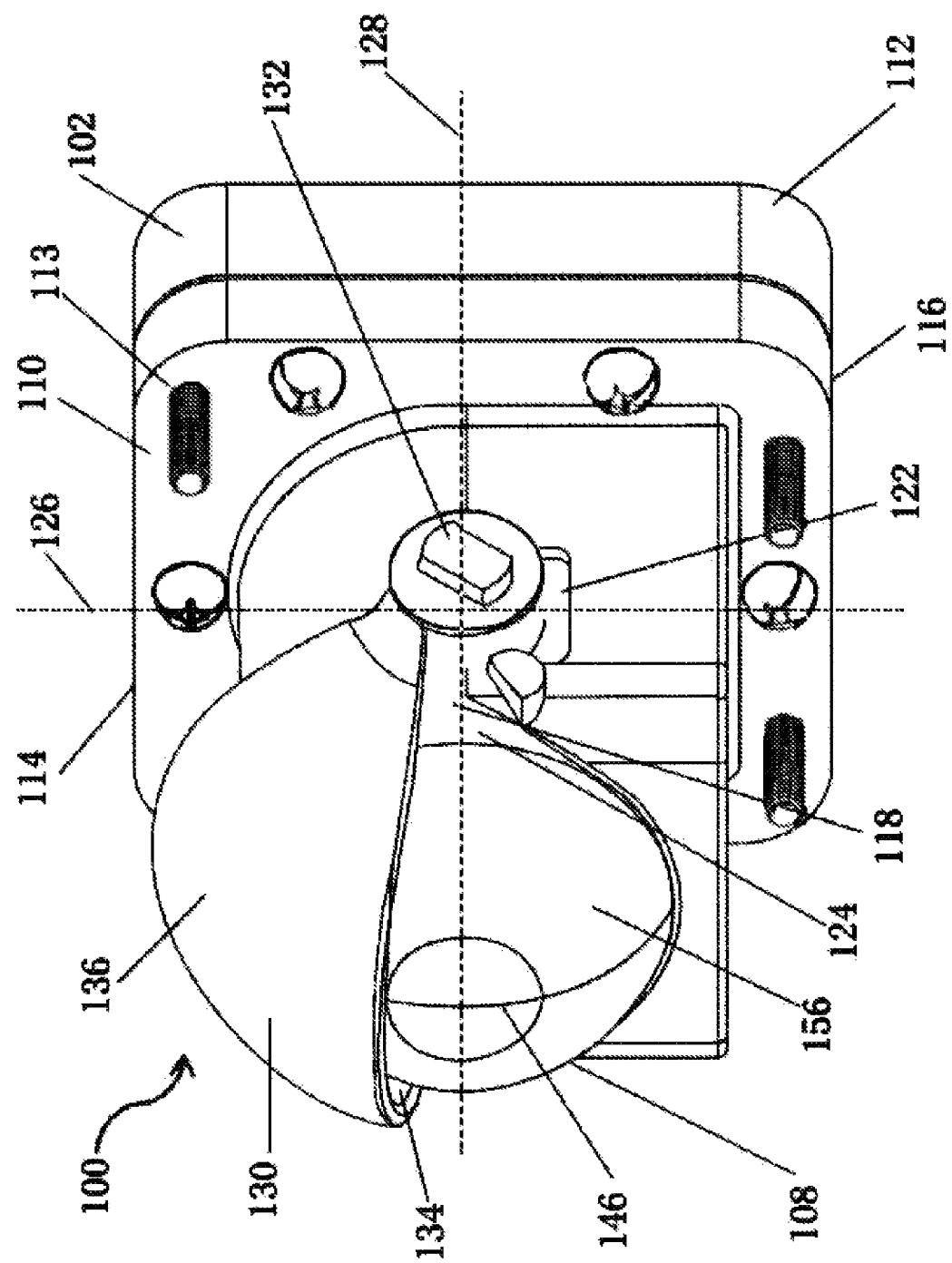
FIG. 1A is a schematic diagram of an eye simulator device according to an embodiment.
Figure 1B:
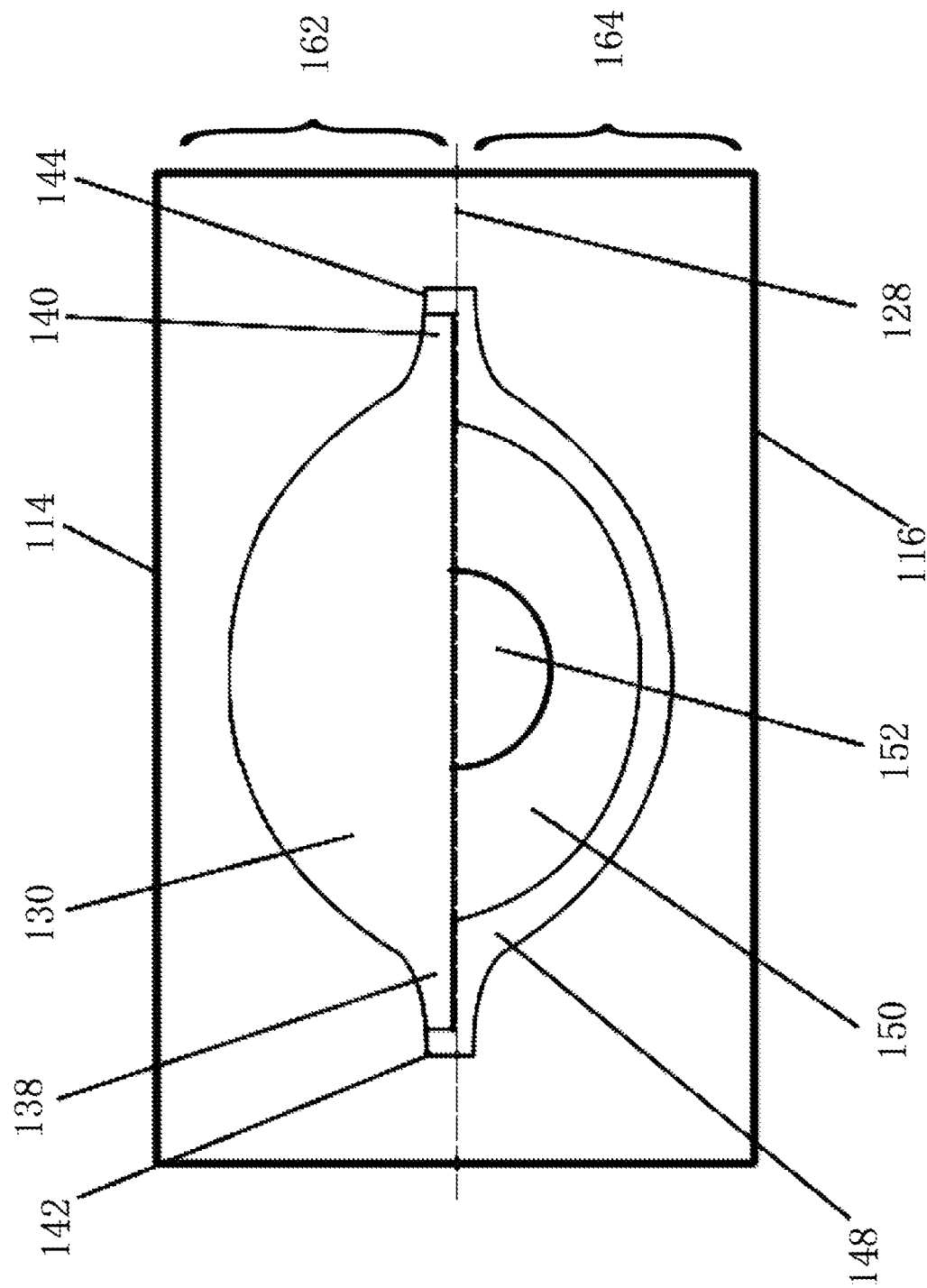
FIG. 1B is a front view of the eye simulator device according to an embodiment.
Figure 1C:
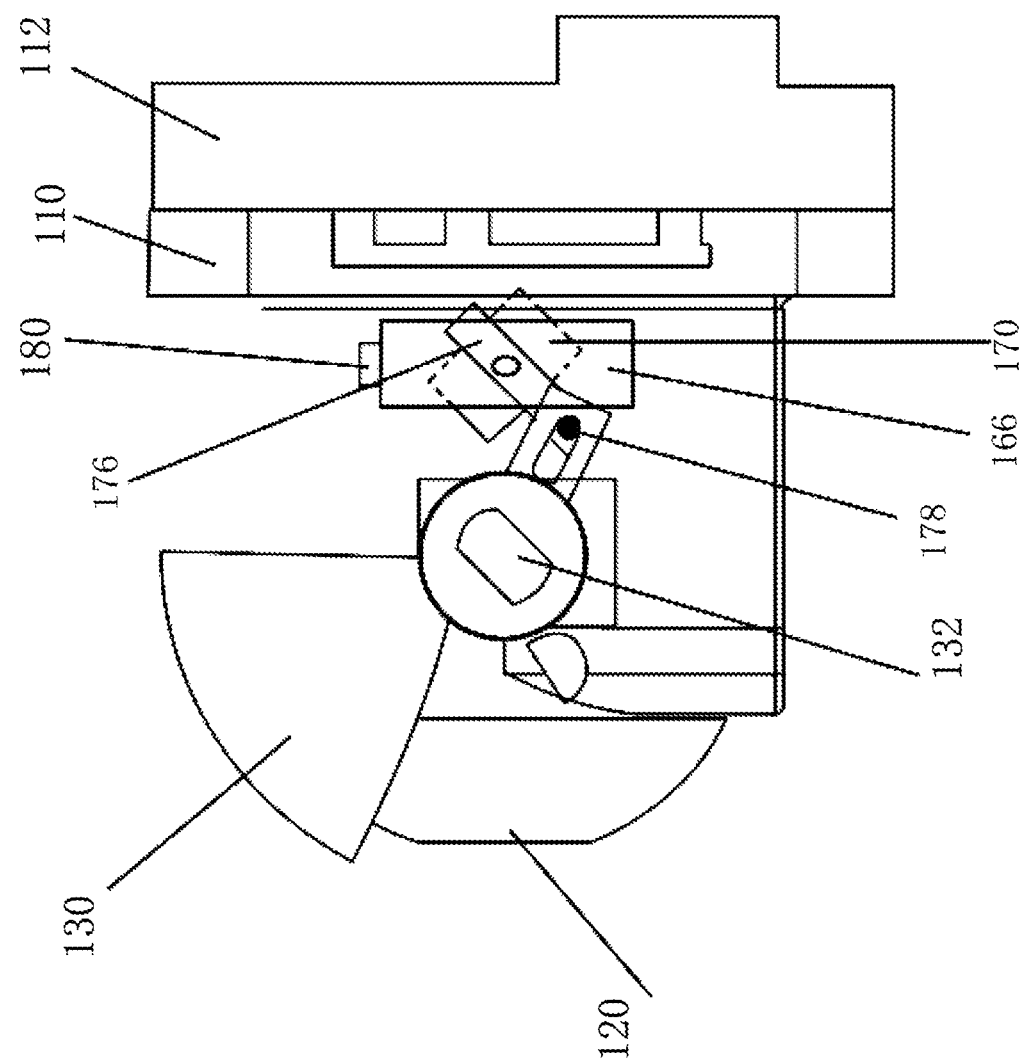
FIG. 1C is right view of the eye simulator device according to an embodiment.
Figure 2:
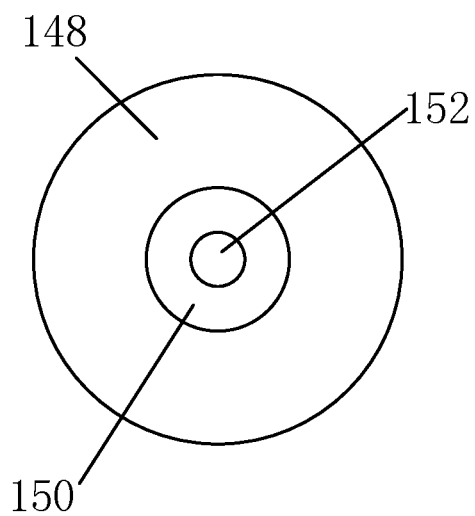
FIG. 2 is schematic diagram of a display to project an image onto or through an eyepiece.
Figure 3A:
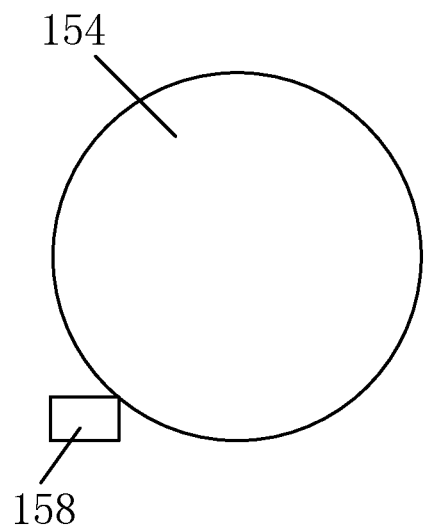
FIG. 3A is a schematic diagram of an image sensor disposed offset from an axis of the display.

Referring to FIGS. 1-3, embodiments may include an eye simulator device 100. The eye simulator device 100 may be used as a stand-alone device. For example, the eye simulator device 100 may be configured as a simulated eye supported by a support 118. Or in the alternative, the eye simulator device 100 may be configured to be part of another device. For example, the eye simulator device 100 may be configured to be incorporated within an eye socket of a mannequin simulator. Embodiments of the eye simulator device 100 may be configured to simulate an eye function (e.g., opening a simulated eyelid, closing the simulated eyelid, blinking, dilating a pupil, and etc.) and an eye condition (e.g., redness to signify irritation, yellowness to signify liver disease, pinkness to signify conjunctivitis, and etc.). Simulating the eye function and the eye condition may be done to facilitate training for medical practitioners.

Embodiments of the eye simulator device 100 may include a base 102. The base 102 may be a structure configured to support components of the eye simulator device 100. In some embodiments, the base 102 may be configured as a housing. The housing may be a structure configured to contain an electrical circuitry 104, an actuator assembly 106, and/or other components while an outer surface of the housing can provide a support for an eyepiece 108 and/or other components. For example, the base 102 may be a housing having a rectangular shape with a base first (front) side 110, a base second (back) side 112, a base top 114, and a base bottom 116. The base first (front) side 110 may be configured to support an eyepiece 108. The base second (back) side 112 may be configured to facilitate attachment to a structure, such as a portion of a mannequin simulator (e.g., to an eye socket portion of the mannequin). This may be achieved via a screw(s) 113 or a similar fastener(s). Alternatively, the base 112 may be configured to allow the eye simulator device 100 to stand upright. The base 102 interior may include the electrical circuitry 104. The base 102 interior may also include the actuator assembly 106. The electrical circuitry 104 and actuator assembly 106 may be in an electrical connection with each other and in an electrical connection with the eyepiece 108. The base 102 may be fabricated from a rigid material, such as metal, plastic, fiberglass, glass, ceramic, and etc.

In some embodiments, the eyepiece 108 may be attached to the base 102 via a support 118. The support 118 may be a structure that is attached to, or attachable to, the base 102. For example, the support 118 may be welded, fastened by screws or other fasteners, glued, snapped via interference fit, and etc. to the base 102. The attachment of the support 118 to the base may be such that the support 118 extends from the base first (front) side 110. The support 118 may be configured to retain a simulated eyeball 120 of the eyepiece 108 and facilitate electrical connection between components of the eyepiece 108 and the electrical circuitry 104. For example, the support 118 may have a support first end 122 and a support second end 124. The support first end 122 may be attached to the base 102 at an opening forming in the base first (front) side 110. The support second end 124 may be configured to retain the simulated eyeball 120. The interior of the support 118 may be hollowed to form a conduit. The conduit may be configured to allow for routing of electrical wiring or some other electrical connectors. This may be done to facilitate electrical connection between the electrical circuitry 104 within the base 102 and at least one component of the eyepiece 108. The support 118 may have a planar square shape at the support first end 122, leading to a post-like shape, and then to a dish or bowl shape at the support second end 124. The dish or bowl shape may be made to complement the shape of the simulated eyeball 120. For example, the support second end 124 may be configured to receive at least a portion of the simulated eyeball 120. In some embodiments, the simulated eyeball 120 and the support 118 may be a unitary structure. In some embodiments, the support 118 may be shaped to resemble an optic nerve and/or a retina like that of a human eye.

In some embodiments, the support 118 can extend from the base first (front) side 110 at an intersection of a base longitudinal axis 126 and a base latitudinal axis 128. For example, the opening in the base first (front) side 110 may be located at the intersection of the base longitudinal axis 126 and the base latitudinal axis 128. While it is contemplated for the support 118 to extend from the base first (front) side 110 at the intersection of the base longitudinal axis 126 and the base latitudinal axis 128, the support 118 may be positioned to extend from other portions of the base 102.

Some embodiments of the eye simulator device 100 may include a simulated eyelid 130. The simulated eyelid 130 may be a member that is pivotally attached to the support 118 by a pivot 132. For example, the simulated eyelid 130 may be pivotally attached to the support first end 122. The pivot 132 may be a rotatable hub assembly, a hinge, a pin-and-barrel configuration, a bushing-and-race configuration, and etc. In some embodiments, the simulated eyelid 130 may have a dome or helmet shape and be configured to cover at least a portion of the simulated eyeball 120. For example, the simulated eyelid 130 have an interior surface of the simulated eyelid 134 and an eyelid exterior surface 136, wherein the simulated eyelid 130 is shaped so that at least the interior surface of the simulated eyelid 134 complements the shape of the simulated eyeball 120. This can facilitate the simulated eyelid 130 being placed over at least a portion of the simulated eyeball 120 (e.g., a portion of the simulated eyeball 120 may fit into the interior surface of the simulated eyelid 134).

In at least one embodiment, the simulated eyelid 130 may include a first side of the simulated eyelid 138 and a second side of the simulated second side of the simulated eyelid 140. Each of the first side of the simulated eyelid 138 and the second side of the simulated eyelid 140 may be pivotally attached to a support first side 142 and a support second side 144, respectively. For example, the first side of the simulated eyelid 138 may be attached to the support first side 142 via a first pivot 132. The second side of the simulated eyelid 140 may be attached to the support second side 144 via a second pivot 132. The pivot 132 connection(s) may be configured to allow the simulated eyelid 130 to be rotated about the pivot(s) 132 while allowing the simulated eyelid 130 to traverse over portions of the simulated eyeball 120. For example, in some embodiments, the simulated eyelid 130 may be rotated about the pivot(s) 132 to cause the simulated eyelid 130 to rotate about an axis defined by the base latitudinal axis 128 or an axis that is parallel to the base latitudinal axis 128. The simulated eyelid 130 may be fabricated from a rigid material, such as metal, plastic, fiberglass, glass, ceramic, and etc. In the alternative, the simulated eyelid 130 may be fabricated from a semi-rigid material, such as a polymer, rubber, silicon, plastic, and etc. In some embodiments, the simulated eyelid 130 may be fabricated form a pliable material.

As described herein, the eyepiece 108 may include the simulated eyeball 120. The simulated eyeball 120 may have a hemispheric shape with a convex shaped front surface 156 configured to mimic an eye of a human. In addition, the simulated eyeball 120 may include features mimicking a simulated lens 146, a sclera 148, an iris 150, a pupil 152, and etc. The simulated eyeball 120 may be fabricated from glass, plastic, ceramic, and etc. The simulated eyeball 120 may be transparent or translucent.

The eyepiece 108 may include a display 154. The display 154 may include a plurality of pixels in an array for generating images. For example, illumination of the pixels in the array can generate various images. The display 154 may be a liquid crystal display ("LCD"), an active-matrix organic light emitting diode ("AMOLED"), and etc. The display 154 may be located within the simulated eyeball 120. The display 154 may be configured to project at least one image onto a convex shaped front surface 156 of the simulated eyeball 120 or through the convex shaped front surface 156 so as to be seen when a user is looking at the convex shaped front surface 156. In some embodiments, the features mimicking the lens 150, the sclera 148, the iris 150, the pupil 152, and etc. may be projections from the display 154. For example, the images may be a 2-dimensional (2D) representation of a human eye or a 3-dimensional (3D), representation of a human eye. In some embodiments, the lens 146 may be an optical element (e.g., glass, ceramic, plastic, and etc.) positioned adjacent the display 154. For example, the lens 146 may be positioned between the display 154 and the eye convex shaped front surface 156. The lens 146 may be configured to converge, diverge, and/or collimate light being emitted from the display 154.

The display 154 may also be configured to generate other images that mimic conditions of the simulated eyeball 120, which may include projecting images to the sclera 148 of the simulated eyeball 120, to mimic a reddening of the sclera (e.g., irritation, conjunctivitis, and etc.), projecting images to the sclera 148 of the simulated eyeball 120, to mimic a yellowing of the sclera (e.g., hepatitis, duct obstruction, liver disease, and etc.), and projecting images to the sclera 148 of the simulated eyeball 120, to mimic a clouding (e.g., glaucoma) of the sclera, and etc. In addition, the display 154 may project images of pupil dilation, project images of pupil miosis, project images of pupil misalignment (i.e., strabismus, amblyopia, and etc.), and etc. In addition, the image sensor 158 may also be configured to track an object motion (e.g., the image sensor 158 may also be a motion sensor). Thus, a medical practitioner can use an object (e.g., a finger, a light pointer, and etc.) to cause the pupil 152 to follow the object. For example, the images of the pupil 152 may be caused to move as the object moves. This may be achieved by the image of the pupil 152 appearing to move as different pixels of the display 154 are illuminated to represent the pupil 152. Thus, a sequence of pixels in the display 154 may be illuminated to generate an appearance of the pupil 152 image to move across the sclera 148. The display 154 may project other images, which may include projecting blood vessels in the sclera 148 for example.

The eyepiece 108 may also include an image sensor 158. The image sensor 158 may be a sensor configured to detect light brightness, light intensity, light motion, wavelengths of light, temperature, pressure and the like, and may record data from the image sensor. For example, the image sensor 158 may be any one or any combination of a photovoltaic sensor, a photodiode, a light-dependent resistor, a proximity light sensor, a thermistor, a resistance thermometer, a thermocouple, a temperature-sensitive semiconductor, a piezoresistive gauge, an optical-strain sensor, a potentiometric sensor, a pressure-sensitive semiconductor, and etc. The data from the image sensor may be transmitted to the electrical circuitry 104 for processing. For example, the data from the image sensor may be transmitted to the driver controller 160 of the electrical circuitry 104. In some embodiments, the image sensor 158 may be co-located with the display 154, i.e., locating at the same position (e.g., being adjacent to each other and occupying a shared space). This may be done to generate the eye simulator device 100 which is configured to mimic conditions of an eye without any moving parts. In some embodiments, the image sensor 158 is disposed offset from an axis of the display 154 (e.g., the line of sight is positioned out of a direct line from the display 154 when watching the display from the convex shaped front surface 156). (See FIG. 3A). The image sensor 158 disposed offset from the axis of the display 154 can provide the advantage of a clear line of sight to the display 154 from the view of the medical practitioner, which may reduce or eliminate any optical interference to the image sensor 158 from light emitted from the display, thereby further facilitating use of an unmodified and readily-available display 154 for the eyepiece 108. In some embodiments, the image sensor 158 is disposed in line with the axis of the display 154 (e.g., positioned directly in front of the display 154 when viewing the display 154 from the convex shaped front surface 156). (See FIG. 3B). This configuration can provide a more realistic visual effect from the medical practitioner's perspective.

Figure 3B:
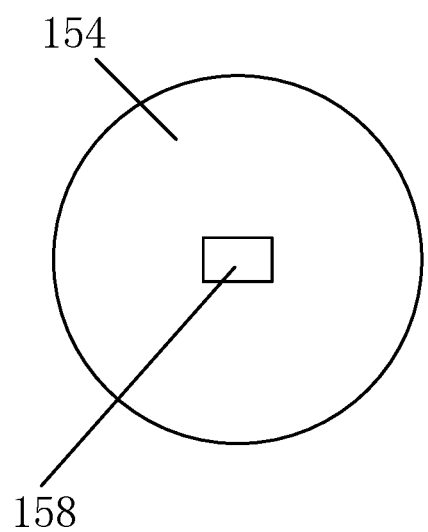
FIG. 3B is a schematic diagram of an image sensor disposed in line with the axis of the display.

Regarding the image sensor 158 being in line with or offset from the axis of the display 154, a line of sight may be defined by a sight-line extending at a normal angle from a central point of the convex shaped front surface 156 of the simulated eyeball 120. If viewing the eye simulator device 100 along the line of sight, an observer would be looking along the sight-line. Looking along the sight-line, an observer would see the image shown in FIG. 1B. The display 154 may be positioned within the simulated eyeball 120 so that it is positioned on this sight-line. In embodiments with the image sensor 158 being in line with the axis of the display 154, the image sensor 158 is also positioned on this sight-line, as shown in FIG. 3B. In embodiments with the image sensor 158 being offset from the axis of the display 154, the image sensor 158 is positioned to not be on this sight-line, as shown in FIB. 3A.

The eye simulator device 100 may also include an actuator assembly 106. The actuator assembly 106 may be attached to or housed within the base 102. For example, the base 102 may be configured as a housing that contains at least a portion of the actuator assembly 106. The actuator assembly 106 may be connected to the electrical circuitry 104 through electrical wiring or electrical connection. The actuator assembly 106 may also be in mechanical connection with the simulated eyelid 130. This may include being in mechanical connection with at least one pivot 132 that the simulated eyelid 130 is connected to. In some embodiments, the actuator assembly 106 may be configured to cause the simulated eyelid 130 to rotate about the pivot(s) 132, cause the simulated eyelid 130 to resist rotation about the pivot(s) 132, cause the simulated eyelid 130 to repeat and reciprocate rotation about the pivot(s) 132, and etc.

The electrical connection in the embodiments of the present disclosure may be wired connection (connection via a wire), and wireless connection (connection via Bluetooth, WIFI and etc.)

For example, the eye simulator device 100 may be segmented into a first sector 162 that is an area extending from the base latitudinal axis 128 to the base top 114, and a second sector 164 that is an area extending from the base latitudinal axis 128 to the base bottom 116. (See FIG. 1B). The actuator assembly 106 may cause the simulated eyelid 130 to rotate about the pivot(s) 132 so that the simulated eyelid 130 (or at least a portion of the simulated eyelid 130) is in the first sector 162. This may be done to mimic eye-opening for the eye simulator device 100 or to generate an operation of opening the simulated eyelid 130. The actuator assembly 106 may cause the simulated eyelid 130 to rotate about the pivot(s) 132 so that the simulated eyelid 130 (or at least a portion of the simulated eyelid 130) is in the second sector 164. This may be done to mimic eye-closure for the eye simulator device 100 or to generate an operation of closing the simulated eyelid 130.

While the simulated eyelid 130 is in the position of eye-opening (or eye-closure), the actuator assembly 106 may be configured to allow the simulated eyelid 130 to be freely moved by manually pulling or pushing the simulated eyelid 130, so that it rotates from the position of eye-opening (or eye-closure) to the position of eye-closure (or eye-opening), or to any position there-between. The actuator assembly 106 may also be configured to resist such motion. The resistance of such motion may be defined by requiring more force to move the simulated eyelid 130, while the simulated eyelid 130 reverting back to the position of eye-opening (or the eye-closure) position if the pulling or pushing is stopped, and etc. In addition, the actuator assembly 106 may cause the simulated eyelid 130 to move to the position of eye-opening (or eye-closure) and from the position of eye-closure (or eye-opening) in a repetitive fashion. This may be done to mimic blinking. In addition, the actuator assembly 106 may cause the simulated eyelid 130 to move from the position of eye-opening to an intermediate position that is between the position of eye-opening and the position of eye-closure. This may be done to mimic squinting. In addition, the actuator assembly 106 may cause the simulated eyelid 130 to move from the position of eye-closure to an intermediate position that is between the position of eye-closure and the position of eye-opening. This may be done to mimic ptosis or blepharoptosis. Other motions of the simulated eyelid 130 may be configured to simulate other eye conditions and other motor functions.

As described above, the eye simulator device 100 may include the display 154. Any one or combination of motions of the simulated eyelid 130 may be used in conjunction with any one or combination of the image projections to simulate an eye function and/or an eye condition. For example, the pupil 152 of the simulated eyeball 120 may be caused to partially dilate while the simulated eyelid 130 may be caused to partially close. This may be done to provide a more realistic squinting simulation. As will be explained later, an application software may be configured to provide instructions for the various components so as to generate scenarios. The squinting described above may be a scenario specified by the software that mimics a flinching reaction when light from a pointer is moved too close (defined by a predetermined distance from the image sensor 158) and at a fast rate towards the image sensor 158.

Figure 4:
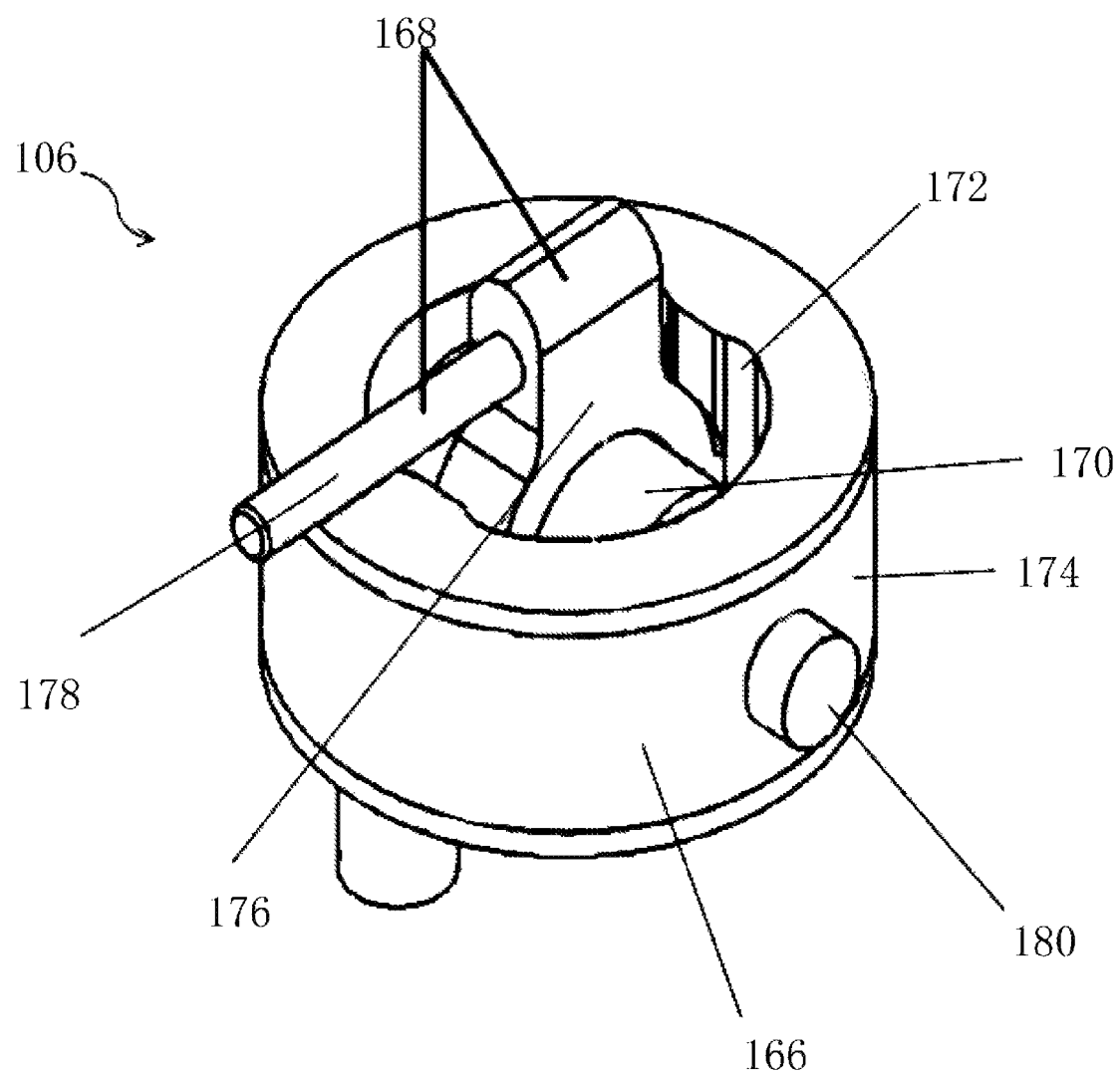
FIG. 4 is a schematic diagram of an actuator assembly that is used with the eye simulator device.
Figure 5:
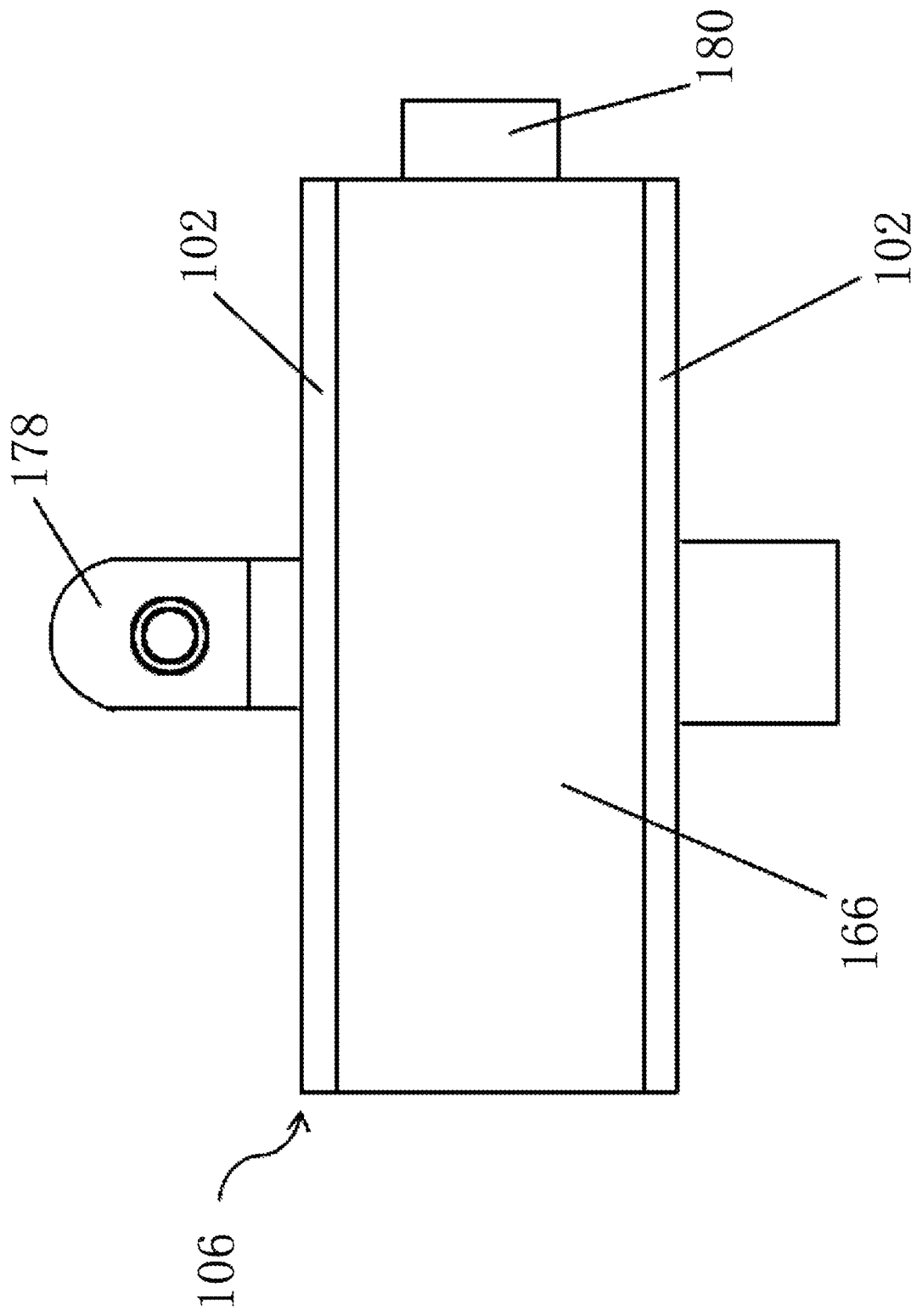
FIG. 5 is a side view an actuator assembly that is used with the eye simulator device.
Figure 6:
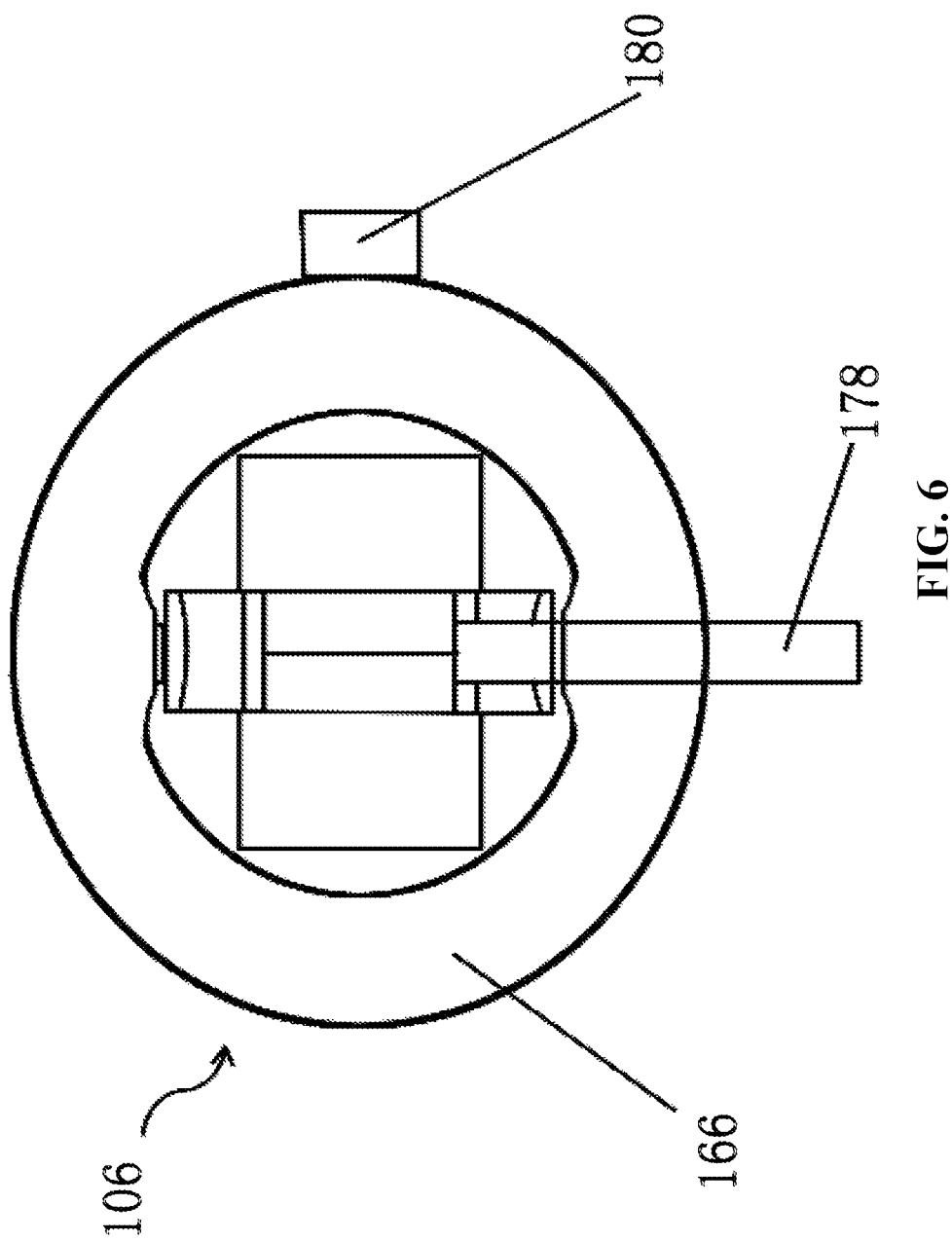
FIG. 6 is a top view of an actuator assembly that is used with the eye simulator device.

Referring to FIGS. 4-6, in at least one embodiment, the actuator assembly 106 may include an electromagnetic ("EM") coil 166. The EM coil 166 may be in an electromechanical connection with an actuator arm 168. For example, the actuator arm 168 may be connected to the EM coil 166 via at least one torque magnet 170. In some embodiments, the EM coil 166 may be a cylindrical object having an EM coil inner surface 172 and an EM coil outer surface 174. The actuator arm 168 and the torque magnet 170 may be positioned within the EM coil 166 so as to be situated at least partially within the EM coil inner surface 172 and be rotatably attached to the EM coil 166.

In some embodiments, the actuator arm 168 may include a connector portion 176 and an arm portion 178. The torque magnet 170 may be sandwiched by the connector portion 176, wherein both the connector portion 176 and the torque magnet 170 may be rotatably attached to the EM coil inner surface 172. The arm portion 178 can extend from the connector portion 176 so that it is positioned outside the EM coil inner surface 172. Electrical signals (e.g., electrical current or electrical voltage) may be applied to the EM coil 166 so as to cause the arm portion 178 to move in a desired direction by torque imposed on the arm portion 178 via the torque magnet 170. The arm portion 178 may be connected to the simulated eyelid 130 and/or the pivot(s) 132 so that motion of the arm portion 178 may cause the simulated eyelid 130 to move about the pivot(s) 132.

In some embodiments, a centering magnet 180 may be attached to the EM coil 166. The centering magnet 180 may be configured to force the arm portion 178 (and the simulated eyelid 130) to move to a default position when there is no electrical signal being applied to the EM coil 166. The default position may be a position at which the simulated eyelid 130 is open or closed, or may be any other position. In addition, or in the alternative, a position sensor 182 may be configured to record an actual position of the simulated eyelid 130 and to transmit the actual position to the driver controller 160. The drive controller 160 may then cause the simulated eyelid 130 to move to a desired position, where the desired position may be defined as a default position defined by the application software, provided the actual position is not the default position and it is in a scenario that the application software is generating the default position desired. The position sensor 182 may be an encoder, a hall effect sensor, and etc.

Figure 7:
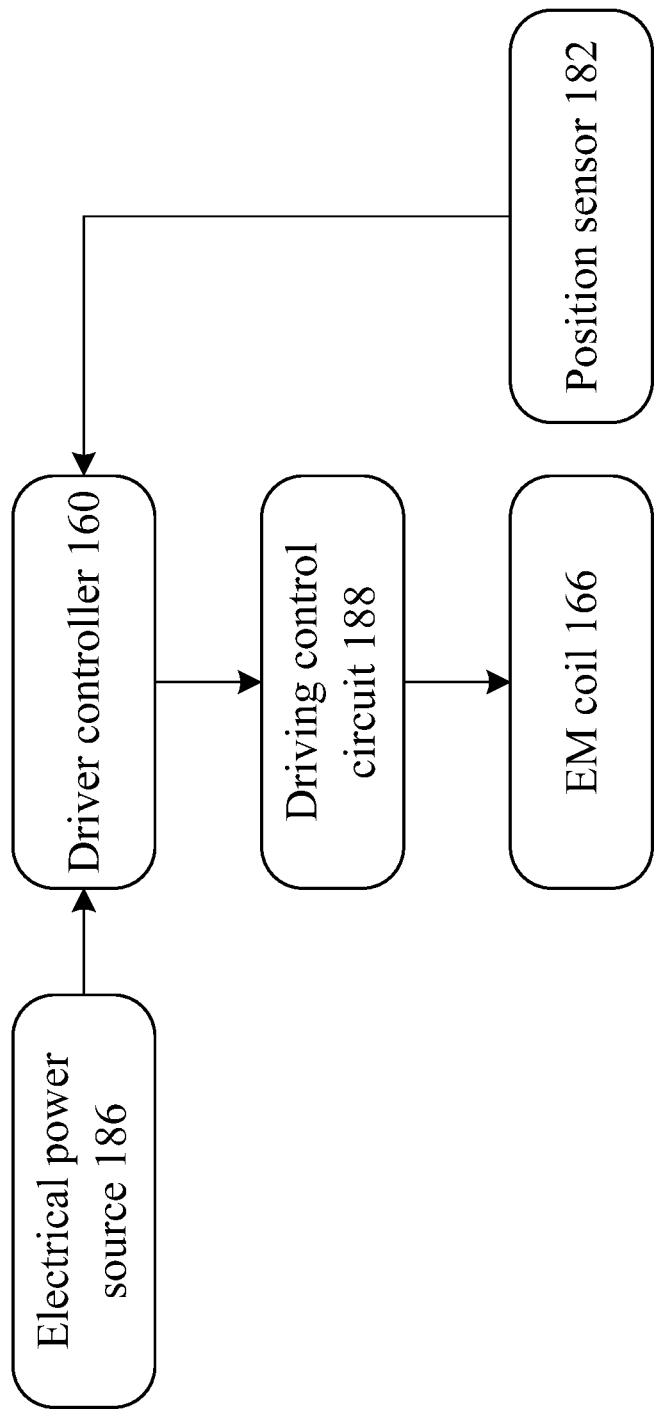
FIG. 7 is an exemplary schematic diagram of an electrical circuitry that is used with the eye simulator device.
Figure 8:
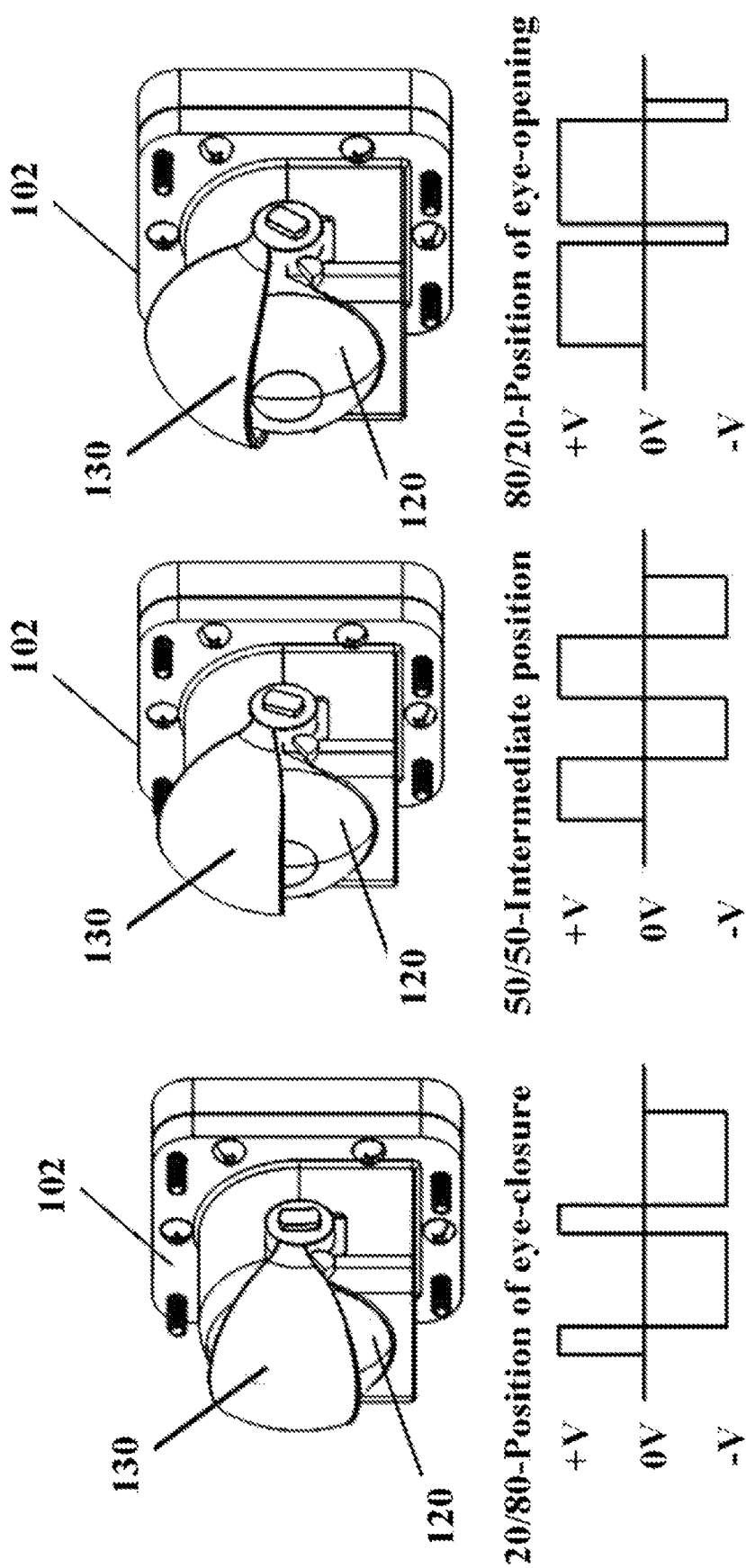
FIG. 8 is a schematic diagram of a simulated eyelid at an eye-closure position, the simulated eyelid at a position that is between an eye-closure position and an eye-opening position (e.g., at an intermediate position), and the simulated eyelid at an eye-opening position.

Referring to FIGS. 7-8, an electrical power source 186 may be configured to supply the electrical power for various components of the eye simulator device 100. The electrical power source 186 may also provide current and/or voltage for generating electrical signals to be sent to the EM coil 166 (via the electrical circuitry 104). In some embodiments, the electrical power source 186 may include a processor. The processor may be configured to receive data from the image sensor and data from the position sensor. The processor may also be configured to transmit position command signals to the electrical circuitry 104. In some embodiments, the processor of the electrical power source 186 may include application software within its memory (e.g., a non-transitory, non-volatile memory in operative association with the processor), and the application software is programmed to cause the processor to execute functions in accordance to medical training scenarios. The processor, in accordance with scenarios of the application software, may generate signals for position commands.

The electrical signals may be generated by the electrical circuitry 104. The electrical circuitry 104 may include at least one integrated circuit. In some embodiments, the electrical circuitry 104 may include a driving control circuit 188. The driving control circuit 188 may contain one or more analog components or digital components, which translate signals for position commands into signal formats that are usable for a driver controller 160, after being configured. The driving control circuit 188 may be a H-bridge motor driver circuit, for example. The driver controller 160 may be a processor (hardware) and/or a module (software) that is for coordinating activities of the various components of the eye simulator device 100. In at least one embodiment, the driving control circuit 188 may be configured to generate a bi-polar pulse with a modulated signal (see FIGS. 8A-8C) that causes the torque magnet 170 to generate torque against the arm portion 178 when the pulse is transmitted to the EM coil 166.

In addition, or in the alternative to the processor of the electrical supply source having the application software, the driver controller 160 may store the application software within its memory (e.g., a non-transitory, non-volatile memory in operative association with a processor of the diver controller 160), and the memory is programmed to cause the driver controller 160 to execute functions in accordance to medical training scenarios. The software application may provide operations for motions of the simulated eyelid 130 and/or the display 154, and the operations are configured to mimic eye conditions for training. Thus, the application software, being executed by the processor(s), may cause the display 154 and/or the actuator assembly 106 to operate in a desired sequence.

In some embodiments, the data from the image sensor may be fed back to the processor(s) to generate a feedback loop by which the eye simulator device 100 provides eye motions and eye conditions that are applicable to treating certain eye conditions and that are reactive to medical practitioner actions. As a non-limiting example, the software application may include instructions to cause the simulated eyelid 130 to move from a position of eye-opening to a position of eye-closure when a light beam at predetermined brightness or intensity (e.g., a flashlight) is detected by an image sensor 158. In such a scenario, the electrical circuitry 104 may generate the bi-polar pulse with the modulated signal to cause the torque magnet 170 to generate a torque against the arm portion 178 to cause the arm portion 178 to move, and thus to force the simulated eyelid 130 to move to the position of eye-closure.

FIG. 8 shows a bi-polar pulse with a modulated signal that may be generated to cause the simulated eyelid 130 to move to a position of eye-closure, a bi-polar pulse with a modulated signal that may be generated to cause the simulated eyelid 130 to move to a position that is between a position of eye-closure and a position of eye-opening (for example, an intermediate position therebetween), a bi-polar pulse with a modulated signal that may be generated to cause the simulated eyelid 130 to move to a position of eye-opening.

As described herein, embodiments of the eye simulator device 100 may provide for resistive motion of the simulated eyelid 130. For example, the image sensor 158 may cause the simulated eyelid 130 to move to a position of eye-closure upon detecting a relatively intense light beam (e.g., light from a flashlight). This may be a scenario mimicking a patient having an extraordinary sensitivity to light, the medical practitioner would want the simulated eyelid 130 open to inspect the eye, and the simulated eyelid would (in a real-life situation) have to be splayed. Thus, the application software may include a scenario in which the actuator arm 168 (and the simulated eyelid 130) may be freely moved from the position of eye-closure by manually pulling or pushing the simulated eyelid 130 so that it rotates from the position of eye-closure to the position of eye-opening, or to any position there-between. But to resist such motion, this may be achieved by the driver controller 160 causing a continuous electrical signal to be transmitted to the EM coil 166 so that the simulated eyelid 130 is continuously biased (otherwise the force is absent) to the position of eye-closure. The medical practitioner not only can splay the simulated eyelid 130, but a release of the simulated eyelid 130 by the medical practitioner would allow the simulated eyelid 130 to move to its biased position of being closed.

It should be noted that the biasing may be to any position, but not just the position of eye-closure. Thus, the medical practitioner can attempt to move the simulated eyelid 130 in any direction until the simulated eyelid 130 is biased to a particular location. One of the benefits of the eye simulator device 100 is the absence of gears (as would be used with electric gear motors) or pumps (as would be used with pneumatic actuators). With embodiments of the eye simulator device 100, when the medical practitioner splays the simulated eyelid 130, no strain is induced on a gear or on a pump since it is the EM coil 166 that is generating the motion of the simulated eyelid 130 or generating the biasing of the simulated eyelid 130. In addition, electric gears or pumps would not be able to cause the simulated eyelid 130 to move or be biased to an intermediate eye position (e.g., a position that is between the position of eye-closure and the position of eye-opening) without some complex and cumbersome mechanical stopping mechanism. With embodiments of the eye simulator device 100, the electrical signal may be configured to cause the actuator arm 168 to move a predetermined distance. The configuration of the electrical signal itself can provide the position at which the actuator arm 178 (and the simulated eyelid 130) will stop or remained biased. In addition, electric gears or pumps would not be able to cause the simulated eyelid 130 to move at different speeds without some type of regulator. With embodiments of the eye simulator device 100, the electrical signal may be configured to cause the actuator arm 168 (and the simulated eyelid 130) to move at a predetermined speed, which can facilitate motions (e.g., blinking v. casually opening or closing of the eye) to be differentiated.

As described above, the eye simulator device 100 may be configured to be incorporated within an eye socket of a mannequin simulator. In some embodiments, the electrical circuitry 104 may be placed into electrical connection or electrical communication (e.g., hardwired connection or wireless connection) with a control system of the mannequin simulator. This can allow simulated operations of the eye simulator device 100 to act in concert with that of the mannequin simulator.

It should be understood that modifications to the embodiments disclosed herein may be made to meet a particular set of design criteria. For instance, the number of or configuration of the base 102, the actuator assembly 106, the eyepiece 108, the EM coil 166, and/or other components or parameters may be configured to meet a particular objective.

It will be apparent to those skilled in the art that numerous modifications and variations of the described examples and embodiments are possible in light of the above teachings of the disclosure. The disclosed examples and embodiments are presented for purposes of illustration only. Other alternative embodiments may include some or all of the features of the various embodiments disclosed herein. For instance, it is contemplated that a particular feature, either individually described or as part of an embodiment described, may be combined with other features described individually, or parts of other embodiments. The elements and acts of the various embodiments described herein can therefore be combined to provide further embodiments.

Therefore, it is the intent to cover all such modifications and alternative embodiments as may fall within the scope of this disclosure. Additionally, the disclosure of a range of values is a disclosure of every numerical value within this range, including end points. Thus, while certain exemplary embodiments of apparatuses and methods for making and using the same have been discussed and illustrated herein, it is to be distinctly understood that the disclosure is not limited thereto but may be otherwise variously embodied and practiced within the scope of the appended claims.

What is claimed is:

1. An eyepiece, comprising:
a simulated eyeball having an eyeball front surface;
a display, configured to project at least one image on or through the eyeball front surface, wherein the at least one image is a 2-dimensional (2D) representation or a 3-dimensional (3D) representation of a human eye; and
a support, configured to hold the eyepiece;
wherein the support is shaped to resemble at least one of an optic nerve of the human eye or a retina of the human eye; and
wherein the support has a support first end and a support second end, a planar square shape at the support first end leads to a post-like shape, a dish shape or a bowl shape is formed at the support second end, and the dish shape or the bowl shape at the support second end complements with a shape of the simulated eyeball.

2. The eyepiece according to claim 1, further comprising:
an image sensor, disposed in line with an axis of the display, or offset from the axis of the display.

3. The eyepiece according to claim 2, wherein the image sensor is configured to detect at least one of light brightness, light intensity, light motion, a light wavelength, temperature, and pressure.

4. The eyepiece according to claim 1, wherein the at least one image comprises at least one of a sclera, an iris, and a pupil.

5. An eye simulator device, comprising the eyepiece according to claim 1, and the eye simulator device further comprises:
a simulated eyelid, pivotally attached to the support and configured to match with the simulated eyeball; and
an actuator assembly, comprising an actuator arm and an electromagnetic (EM) coil in connection with the actuator arm, the actuator arm being in a mechanical connection with the simulated eyelid so as to drive the simulated eyelid to generate an eye motion.

6. The eye simulator device according to claim 5, further comprising:
a base, being a housing of the actuator assembly, wherein the support extends from the base.

7. The eye simulator device according to claim 5, further comprising: an electrical circuitry, in connection with the actuator assembly and the display and configured to generate a bi-polar pulse with a modulated signal.

8. The eye simulator device according to claim 7, further comprising: a position sensor configured to record a position of the simulated eyelid and to transmit the position of the simulated eyelid to the electrical circuitry.

9. The eye simulator device according to claim 5, further comprising:
a centering magnet configured to force the actuator arm to a default position.

10. A mannequin simulator, comprising at least one eye simulator device according to claim 5, and the eye simulator device is arranged in at least one eye socket of the mannequin simulator.

11. A training method for a medical practitioner, comprising:
providing the eye simulator device according to claim 5;
projecting at least one image to the eyepiece to generate an eye condition via the display, wherein the at least one image is a 2-dimensional (2D) representation or a 3-dimensional (3D) representation of a human eye and comprises at least one of a sclera, an iris, and a pupil, and the eye condition comprises one of a reddening of the sclera, a yellowing of the sclera, and a cloudiness of the sclera;
driving the actuator assembly to cause the simulated eyelid to generate an eye motion, wherein the eye motion comprises one of eye closing, eye opening, eye blinking, and position offsetting of the simulated eyelid; and causing the display to generate a pupil motion by using an image sensor to tracking an object motion.

12. The training method for a medical practitioner according to claim 11, further comprising:

in response to an operation of an operator, causing the display to generate the eye condition, causing the simulated eyelid to generate the eye motion; and causing the display to generate the pupil motion.

* * * * *